(12) United States Patent
Feng et al.

(10) Patent No.: US 9,029,130 B2
(45) Date of Patent: May 12, 2015

(54) UNITARY PLASTIC CONDUCTIVITY SENSOR

(75) Inventors: Chang-Dong Feng, Long Beach, CA (US); Barry W. Benton, Orange, CA (US)

(73) Assignee: Rosemount Analytical Inc., Irvine, CA (US)

( * ) Notice: Subject to any disclaimer, the term of this patent is extended or adjusted under 35 U.S.C. 154(b) by 0 days.

(21) Appl. No.: 13/325,265

(22) Filed: Dec. 14, 2011

(65) Prior Publication Data

US 2012/0178151 A1    Jul. 12, 2012

Related U.S. Application Data

(60) Provisional application No. 61/423,281, filed on Dec. 15, 2010.

(51) Int. Cl.
*C12M 1/34* (2006.01)
*C12M 3/00* (2006.01)
*C12M 1/00* (2006.01)
*C12M 1/36* (2006.01)
*C12M 1/38* (2006.01)
*C12N 9/00* (2006.01)
*C12N 11/00* (2006.01)
*G01N 27/07* (2006.01)
*G01N 27/30* (2006.01)

(52) U.S. Cl.
CPC ............... *G01N 27/07* (2013.01); *G01N 27/30* (2013.01)

(58) Field of Classification Search
USPC ................ 435/283.1–309.4; 204/403.01
See application file for complete search history.

(56) References Cited

U.S. PATENT DOCUMENTS

| 5,704,118 | A | 1/1998 | Kaneko et al. ................ 29/874 |
| 6,334,767 | B2* | 1/2002 | Kieras et al. ................ 425/392 |
| 7,323,887 | B2 | 1/2008 | Feng ............................ 324/724 |
| 7,772,854 | B2 | 8/2010 | Rezvani ....................... 324/691 |
| 2006/0011474 | A1* | 1/2006 | Schulein et al. .......... 204/403.01 |
| 2010/0326842 | A1* | 12/2010 | Mazza et al. .............. 205/777.5 |
| 2010/0331728 | A1* | 12/2010 | Zhang et al. ................ 600/583 |

FOREIGN PATENT DOCUMENTS

| CN | 1768261 A | 5/2006 |
| WO | WO 2005/057168 | 6/2005 |
| WO | WO 2007/107844 | 9/2007 |
| WO | WO 2010/103174 | 9/2010 |

OTHER PUBLICATIONS

International Search Report and Written Opinion from corresponding International patent application No. PCT/US2011/065028 dated Mar. 29, 2012.

(Continued)

*Primary Examiner* — Nathan Bowers
*Assistant Examiner* — Lydia Edwards
(74) *Attorney, Agent, or Firm* — Christopher R. Christenson; Kelly, Holt & Christenson, PLLC (57) ABSTRACT

A contacting-type conductivity sensor includes an electrically-insulative plastic body and a plurality of electrodes. The plurality of conductive electrodes is disposed in the plastic body. Each electrode is constructed of plastic and fused with the electrically-insulative plastic body. A method of manufacturing the conductivity sensor is provided along with a single-use bioreactor employing the sensor.

16 Claims, 5 Drawing Sheets

(56) References Cited

OTHER PUBLICATIONS

"Conductive Compounds for Medical Applications: Computerized Thermoplastic Solutions". Technical Brief from RTP co. Imagineering Plastics.

Office Action for counterpart Canadian Patent Application No. 2,821,332 dated Dec. 18, 2014, 6 pages.

First Office Action from Chinese Application No. 201210122268.3 dated Sep. 30, 2014, 11 pages.

* cited by examiner

UNITARY PLASTIC CONDUCTIVITY SENSOR

CROSS-REFERENCE TO RELATED APPLICATION

The present application is based on and claims the benefit of U.S. provisional patent application Ser. No. 61/423,281, filed Dec. 15, 2010, the content of which is hereby incorporated by reference in its entirety.

BACKGROUND

Liquid conductivity measurement systems are used for measuring the conductivity of water and aqueous or non-aqueous solutions in environmental, medical, industrial, and other applications where an indication of the ionic content of the liquid is required.

Liquid conductivity is measured in a variety of contexts to provide a parameter that can be related to bulk ionic concentration. In situations where a single type of ion is present, the conductivity can actually be related to the specific ionic concentration. Even in situations where a number of different ionic compounds are present, the measurement of bulk liquid conductivity can still provide very useful information. Accordingly, there has been widespread adoption and utilization of conductivity measurement by the industry for a variety of different purposes.

Figure 1:
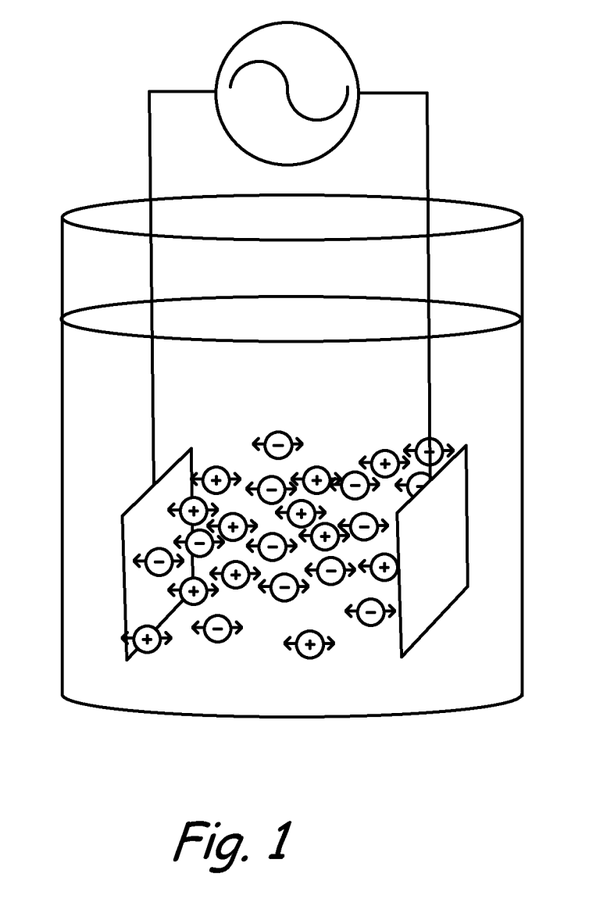
FIG. 1 is a diagrammatic view of a contact-type conductivity measurement system with which embodiments of the present invention are particularly useful.

Typically, contact-based conductivity measurement systems include a conductivity cell and an associated conductivity meter. FIG. 1 illustrates such a system. A conductivity meter generates an AC voltage that is applied to the electrodes of the conductivity cell. The meter then senses the resultant current flow between the electrodes of the cell. This current is generally a function of the conductivity of the liquid to which the cell is exposed.

The amount of current that flows between the electrodes depends not only the solution conductivity, but also on the length, surface area, and geometry of the sensor electrodes. The probe constant (also called sensor constant or cell constant) is a measure of the current response of a sensor to a conductive solution, due to the sensor's dimensions and geometry.

Contact-type conductivity sensors are generally made from at least two pairs of metallic electrodes spaced apart in an insulating sensor body. The distance between and surface area of the electrodes are defined. During operation, the electrodes are in direct contact with the sample solution. The conductivity of the sample solution can be measured by using either a two-electrode or a four-electrode method.

Conventional manufacturing methods rely on metal in the form of thin/thick film, or a rod as the electrode, and plastic, or ceramic/glass, as the sensor body materials. Issues have risen with conventional manufacturing methods including cost and leakage between the seal and sensor body materials.

Providing a contact-type conductivity sensor that is not only lower cost than previous contacting-type conductivity sensors, but more resistant to leaks that would represent a significant advance for contact-type conductivity sensors.

SUMMARY

A contacting-type conductivity sensor includes an electrically-insulative plastic body and a plurality of electrodes. The plurality of conductive electrodes is disposed in the plastic body. Each electrode is constructed of plastic and fused with the electrically-insulative plastic body. A method of manufacturing the conductivity sensor is provided along with a single-use bioreactor employing the sensor.

DETAILED DESCRIPTION OF ILLUSTRATIVE EMBODIMENTS

Figure 2:
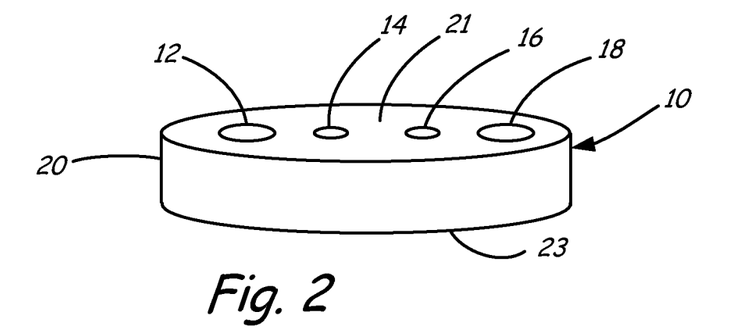
FIGS. 2 and 3 are perspective and top plan views of a monolithic plastic conductivity sensor in accordance with an embodiment of the present invention.
Figure 3:
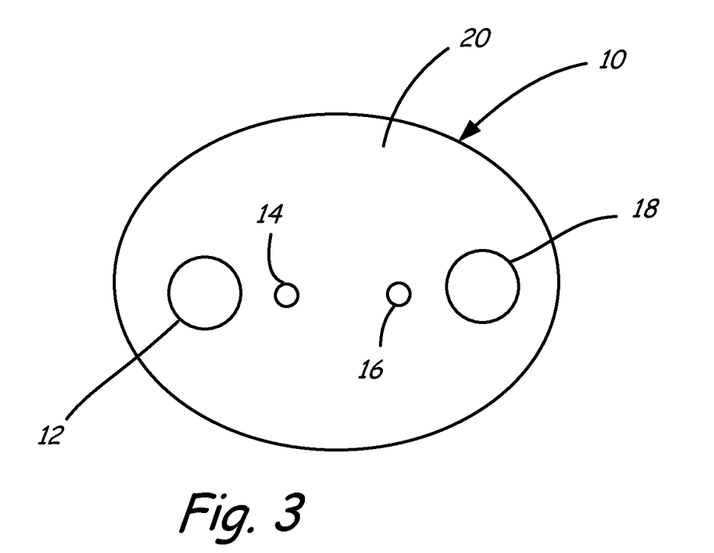

FIGS. 2 and 3 are perspective and top plan views of a unitary plastic conductivity sensor 10 in accordance with an embodiment of the present invention. As used herein "plastic" is intended to mean a synthetic organic polymer that can be molded into shape while soft and then set into a rigid or slightly elastic form. Sensor 10 includes at least two and preferably four conductive electrodes 12, 14, 16, 18 disposed within insulative sensor body 20. Sensor body is illustrated having a pair of opposing faces 21, 23 and a sidewall extending therebetween. Each of conductive electrodes 12, 14, 16, 18 extends from first face 21 through sensor body 20 to second face 23. In use, one of faces 21, 23 will be in direct contact with a sample solution to determine the conductivity of the sample solution. As illustrated in FIG. 3, when four electrodes are used, they are preferably collinear with one another.

The entire conductivity sensor 10 is considered unitary in that the entire sensor is constructed of plastic with no seals or material interfaces therein. Instead, the whole sensor 10 is a single plastic piece with portions thereof (electrodes 12, 14, 16, 18) being electrically conductive. Each of electrodes 12, 14, 16, 18, and sensor body 20 are preferably formed of a thermoplastic compound where additives, or other suitable materials are provided in the regions of electrodes 12, 14, 16, 18 to provide conductivity.

Conductive plastic compounds, such those used for electrodes 12, 14, 16, 18 are known and readily available. Some exemplary compounds are sold by RTP Company of Winona, Minn. The electrically conductive thermoplastic compounds available from RTP Company generally include a resin that has been modified with conductive additives, including carbon-based (powder and fibers), metal-based (solids and coatings), and all-polymerics. Compounds have been developed based in polyethylene, polypropylene, and polystyrene. Generally, such materials are used for electrostatic discharge (ESD) control with tuning capability, and mechanical properties similar to the matrix resin, and processing ease. Another all-polymeric available from RTP is sold under the trade designation Permastat PS®. Permastat products are non-sloughing, colorable, and available in a wide array of polymers.

Many different plastic organic polymers can be compounded with conductive fillers to render them conductive. Such polymeric compounds include acetal (POM), acrylic (PMMA), fluoroplastics (PTFE, PVDF, PFA), polycarbonates (PC), polyetheretherketone (PEEK), polyolefins (polypropylene, polyethylene, polymethylpentene), polysulfone (PSU), polyethersulphone (PEC), polyurethane elastomer (TPU), and styrenics (polystyrene, ABS). Preferably, the polymeric compound used for both sensor body 20 and the electrode regions is a thermoplastic. However, any suitable polymer can be used. Thermoplastics provide an important advantage, however, in that the sensor body and electrodes can be provided separately, assembled together, and heated to the thermoplastic melting point at which time all material interfaces fuse together to form a unitary whole. Thus, sensor body 20 is preferably a disc or rod that is drilled or bored to generate apertures that can receive rods that will form electrodes 12, 14, 16, 18. With rods placed within the suitable bores, the entire assembly is simply heated to the thermoplastic melting point of the sensor body and electrodes to form a unitary plastic whole. The entire assembly can then be sliced, to provide individual unitary plastic conductivity sensors 10.

Figure 4:
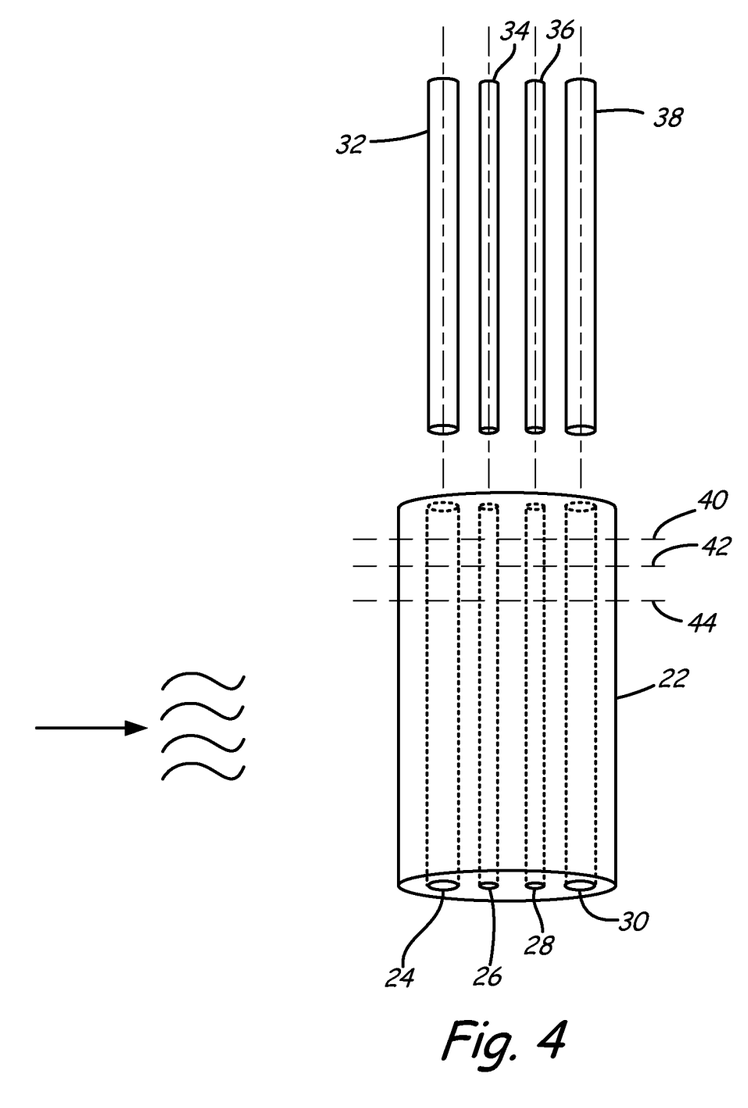
FIG. 4 is a diagrammatic view of a manufacturing process for the conductivity sensor shown in FIGS. 2 and 3.

FIG. 4 is a diagrammatic view of a manufacturing process for conductivity sensor 10 (shown in FIGS. 2 and 3). A rod 22 of electrically insulative plastic material is provided having a number of bores 24, 26, 28, and 30. Generation of bores 24, 26, 28, and 30 in rod 22 can be performed in any suitable manner including drilling. However, bores 24, 26, 28, and 30 can also be pre-formed in body 22 in a casting or extrusion-type process.

Conductive plastic 32, 34, 36, 38, is injected or otherwise conveyed into respective bores 24, 26, 28, 30. By injecting plastic 32, 34, 36, and 38 into respective bores, while the plastic is at a temperature above its glass transition temperature, the plastic will flow through each respective bore to fill the contours therein. Once cooled, a unitary plastic whole is formed. In one embodiment, body 22 and plastic portions 32, 34, 36, 38 are formed of the same plastic compound such as acrylic, ABS, carbonate, or others. The only difference between the materials of body 22 and rods 32, 34, 36, 38 is the presence of a conductive additive provided during the formation of rods 32, 34, 36, 38 to render such rods electrically conductive.

In any event, after the plastic 32, 34, 36, 38 has been injected into respective bores and cooled, an entirely-plastic unitary article is manufactured. Individual conductivity sensors can be formed by cutting the article, for example, along cut lines 40, 42, 44, et cetera.

Although the manufacturing process set forth above with respect to FIG. 4 is illustrated with respect to inserting a number of electrically-conductive rods into an insulative plastic body and heating the body to a glass transition temperature of at least the rods or the plastic body, embodiments of the present invention can be practiced using other manufacturing methods as well. For example, embodiments can be practiced wherein the entire assembly is simply provided as a single complex extrusion. In such extrusion, the conductive plastic is fed in the regions which will thereafter become electrodes, to generate the fused assembly as a result of the extrusion process. Then, individual plastic conductivity sensors can be individually cut from the extruded whole.

Although the embodiment described with respect to FIG. 4 injected plastic into the bores of insulative body 22, embodiments of the present invention can also be practiced where insulative body 22 is injected around a plurality of conductive plastic rods while such rods are held or maintained in a mold or other suitable structure.

Figure 5:
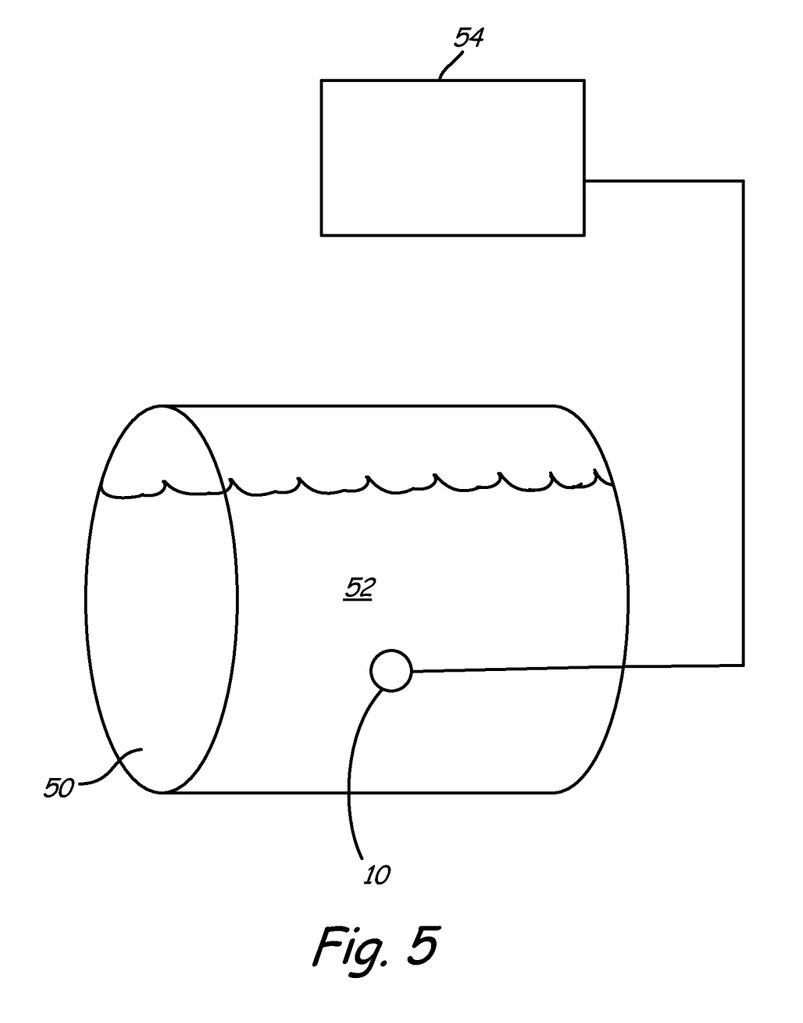
FIG. 5 is a diagrammatic view of a solid plastic conductivity sensor being used to measure the conductivity of a solution within a single-use bioreactor in accordance with an embodiment of the present invention.

FIG. 5 is a diagrammatic view of a solid plastic conductivity sensor being used to measure the conductivity of a solution within a single-use bioreactor or container in accordance with an embodiment of the present invention. As used herein, single-use bioreactor or container 50 is intended to be any plastic container that is of such low cost as to be essentially disposable for processes such as bioreaction. Conductivity sensor 10 is mounted within single-use bioreactor 50 and the electrodes of sensor 10 are in contact with a specimen 52 disposed within single-use bioreactor 50. Sensor 10 is coupled via a two or four-wire connection to conductivity analyzer 54 which provides suitable energization signals to sensor 10. Analyzer 54 measures conductivity of specimen 52 using sensor 10 and provides a read-out or other suitable indication of the conductivity of the specimen 52.

One particular synergy provided by embodiments of the present invention is due to the extremely low cost required to manufacture sensor 10. The cost can be driven down to such an extent that sensor 10 can be considered disposable. Thus, the entire single-use bioreactor and sensor 10 can be disposed of after the bioreaction is complete. In this sense, sensor 10 may be considered a single-use plastic conductivity sensor.

Figure 6:
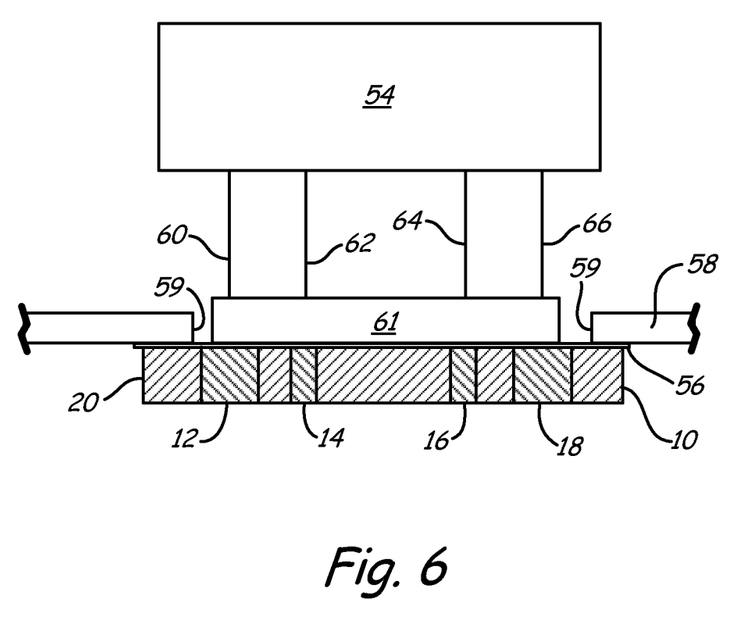
FIG. 6 is cross-sectional diagrammatic view of a plastic conductivity sensor mounted to a portion of a plastic wall of a single-use bioreactor in accordance with an embodiment of the present invention.

FIG. 6 is cross-sectional diagrammatic view of a plastic conductivity sensor mounted to a portion of a plastic wall of a single-use bioreactor in accordance with an embodiment of the present invention. Wall 58 is constructed of a plastic that is bonded, either using thermal or adhesive-based bonding to single-use plastic conductivity sensor 10 at reference numeral 56. Wall 58 defines a sealable bioreaction chamber therein. Aperture 59 is created in wall 58 to allow conductors 60, 62, 64, and 66 to pass therethrough. However, bond or weld 56 creates a liquid-tight seal between sensor 10 and wall 58. While FIG. 6 shows single-use conductivity sensor 10 bonded to a wall of a single-use bioreactor, any other plastic container that requires conductivity measurement can be employed in accordance with embodiments of the present invention.

In the embodiment shown in FIG. 6, conductivity analyzer 54 is coupled to electrodes 12, 14, 16, 18 via respective wires, or conductors, 60, 62, 64, 66. Each of conductors 60, 62, 64, 66 makes electrical contact with a respective electrode 12, 14, 16, 18 through connector 61. The embodiment illustrated with respect to FIG. 6 is a four-wire embodiment in that conductivity analyzer 54 creates an electrical current or voltage between electrodes 12 and 18 and then uses electrodes 14 and 16 to measure the electrical response of the specimen or solution therein. It is also known to use a single pair of electrodes for conductivity measurements.

Although the present invention has been described with reference to preferred embodiments, workers skilled in the art will recognize that changes may be made in form and detail without departing from the spirit and scope of the invention.

What is claimed is:
1. A single-use bioreactor comprising:
   a contacting-type conductivity sensor comprising:
     an electrically-insulative thermoplastic body;
     a plurality of conductive electrodes disposed in the plastic body, wherein each electrode is constructed of thermoplastic and co-extruded with the thermoplastic body; and
     wherein the electrically-insulative thermoplastic body and the plurality of conductive electrodes are formed of the same type of plastic and co-extruded such that the sensor is extruded as one seamless object with no material interfaces between the body and the electrodes and such that each conductive electrode com- prises the same thermoplastic material as the electrically-insulative thermoplastic body;
a plastic bioreaction chamber configured to hold a specimen; and
wherein the sensor is mounted within the plastic bioreaction chamber such that the electrodes of the contactin e conductivity sensor are configured to contact the specimen and such that the sensor seals an aperture within a wall of the plastic bioreaetion chamber.

2. The single-use bioreactor of claim 1, wherein the plurality of electrodes includes four electrodes.

3. The single-use bioreactor of claim 2, wherein the electrodes are collinear.

4. The single-use bioreactor of claim 1, wherein the electrically-insulative thermoplastic body is formed in the shape of a disc having a pair of opposing faces, and wherein each electrode extends from the first through the thermoplastic body to the other face.

5. The single-use bioreactor of claim 4, wherein one of the faces is configured to be exposed to a sample solution to measure conductivity of the sample solution.

6. The single-use bioreactor of claim 1, wherein at least some of the electrodes have different diameters than other electrodes.

7. The single-use bioreactor of claim 6, wherein a plurality of electrodes have a larger diameter than a plurality of other electrodes.

8. The single-use bioreactor of claim 7, wherein the plurality of other electrodes is disposed between the plurality of electrodes having the larger diameter.

9. The single-use bioreactor of claim 8, wherein all electrodes are substantially collinear with one another.

10. The single-use bioreactor of claim 1, wherein the conductivity sensor comprises a conductive additive compound.

11. The single-use bioreactor of claim 10, wherein the conductive additive comprises a carbon-based additive.

12. The single-use bioreactor of claim 10, wherein the conductive additive comprises a metal-based additive.

13. The single-use bioreactor of claim 10, wherein the conductive additive comprises an all-polymerics additive.

14. A method of forming a unitary plastic conductivity sensor for a single-use bioreactor, the method comprising:
providing a non-conducting plastic body;
generating a plurality of apertures in the plastic body;
providing a molten conductive plastic material into each of the plurality of apertures, such that the molten conductive plastic material, upon solidification, comprises a conductive plastic rod formed of the same material as the plastic body;
heating the non-conducting plastic body and the plurality of conductive rods to bond the plurality of conductive rods to the non-conducting body without any material interfaces to form the unitary plastic conductivity sensor; and
wherein the non-conducting plastic body is configured such that it attaches to and seals an aperture within a wall of a plastic bioreactor such that the unitary plastic conductivity sensor in contact with a space inside the single-use bioreactor, wherein the space inside the single-use bioreactor is configured to hold a specimen for conductivity testing.

15. The method of claim 14, and further comprising slicing the assembly into a plurality of discrete plastic conductivity sensors.

16. A single-use bioreactor manufactured by the process of claim 14.

* * * * *

UNITED STATES PATENT AND TRADEMARK OFFICE
CERTIFICATE OF CORRECTION

| | | |
|---|---|---|
| PATENT NO. | : 9,029,130 B2 | Page 1 of 1 |
| APPLICATION NO. | : 13/325265 | |
| DATED | : May 12, 2015 | |
| INVENTOR(S) | : Chang-Dong Feng et al. | |

It is certified that error appears in the above-identified patent and that said Letters Patent is hereby corrected as shown below:

In the Claims

Column 5, Claim 1:
Line 6:

remove "contactin e" and insert --contacting-type--

Column 5, Claim 4:
Line 17:

remove "first through" and insert --first face through--

Column 6, Claim 14:
Line 24:

remove "sensor in" and insert --sensor is in--

Signed and Sealed this
First Day of March, 2016

Michelle K. Lee
*Director of the United States Patent and Trademark Office*